Feb. 17, 1953 E. S. BOERNER Plant Pat. 1,169
CHRYSANTHEMUM PLANT
Filed April 29, 1952
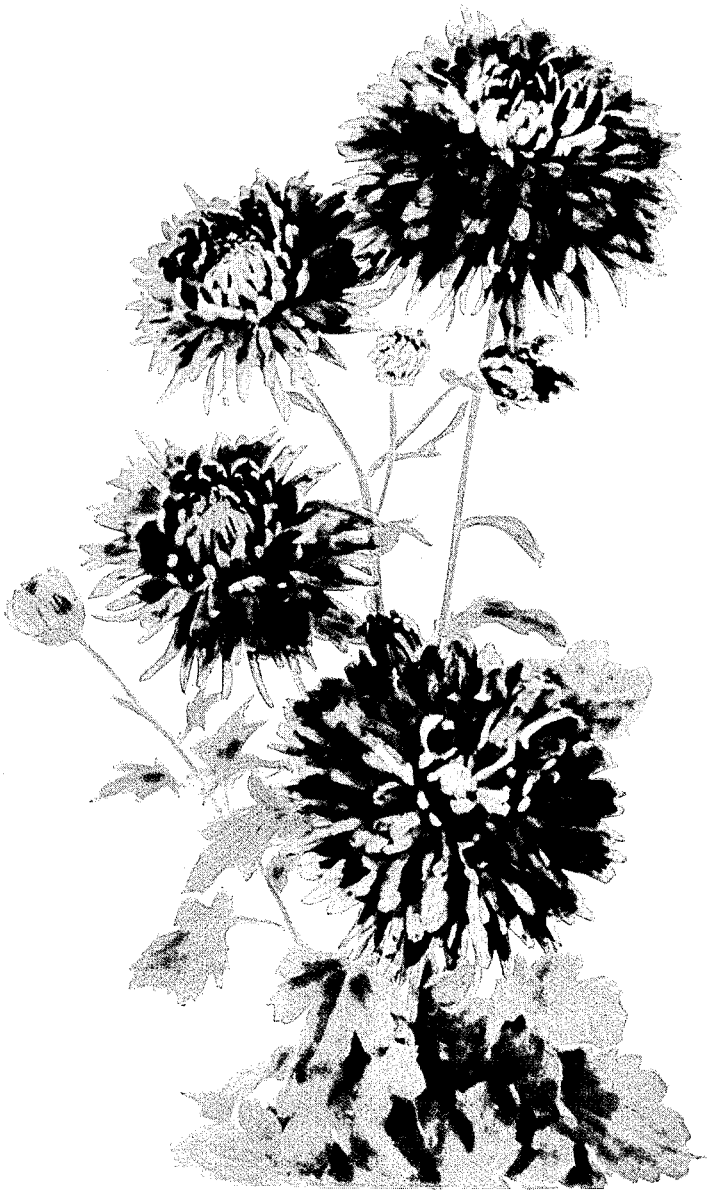
Inventor.
E. S. Boerner
By: Robert Robb
Attorneys.

Patented Feb. 17, 1953

Plant Pat. 1,169

UNITED STATES PATENT OFFICE 1,169

CHRYSANTHEMUM PLANT

Eugene S. Boerner, Newark, N. Y., assignor to Jackson & Perkins Company, Newark, N. Y., a corporation of New York Application April 29, 1952, Serial No. 284,924

1 Claim. (Cl. 47—60)

The present invention relates to a new and distinct variety of chrysanthemum plant of the incurved type, which was originated by me by crossing the unpatented variety "Maroon 'n Gold" with an unnamed and unpatented variety known as "4408-5 Indiana Seedling."

The primary objective of this cross-breeding was to produce a new variety that is a larger and earlier form of the popular variety "Maroon 'n Gold." This objective was fully achieved, as evidenced by the fact that the flowers of my new variety are larger than those of "Maroon 'n Gold" and the blooming period is earlier, as hereinafter more particularly pointed out. In addition, the color of the flowers of my new variety is deeper than that of the parent "Maroon 'n Gold." These characteristics, when considered in combination with each other, clearly distinguish the new variety from its parents, as well as from all other varieties of chrysanthemums.

Asexual reproduction of my new variety by both top cuttings and by underground runners, at Newark, New York, shows that the foregoing characteristics and distinctions come true to form and are established and transmitted through succeeding propagations.

The accompanying drawing shows typical specimens of the new variety, with the flowers and foliage in different stages of development.

The following is a detailed description of the new variety, as observed in fields at Newark, New York, in the early part of the month of September and in the early part of the morning, with color terminology in accordance with Ridgway's Color Standards and Nomenclature:

Parentage: "Maroon 'n Gold" × "4408-5 Indiana Seedling."

Classification: Incurved type.

Growth: Upright; bushy; attains a height of from 3½ to 4 feet.

Cold resistance: Plant is very winter hardy in northern New York; flowers are frost resistant, as determined by comparison with other varieties grown under comparable conditions.

Blooming habit: In Newark, New York, climatic area, date of start of bloom is about September 1st, and blooms continue until frost.

Bud:

*Color.*—When sepals first divide—Victoria Lake, Plate 1. When petals begin to unfurl—Oxblood Red, Plate 1. When half blown: inside of petals—Nopal Red, Plate 1, lightly overcast with Carmine, Plate 1; reverse of petals—Pale Lemon Yellow, Plate 4, lightly overcast with Nopal Red, Plate 1, in the upper half of the petals.

*Peduncle.*—Color—Light Cress Green, Plate 31. Strength—strong.

Bloom:

*Size.*—4 to 4½ inches.

*Stem.*—Strong.

*Form.*—Incurved.

*Petalage.*—Double.

*Color.*—Center of flower—Reflexed petals Nopal Red, Plate 1, lightly overcast with Pinard Yellow, Plate 4. Outer petals—Brazil Red, Plate 1, lightly overcast with Nopal Red, Plate 1. Base of petals—Light Greenish Yellow, Plate 5. Inside of petals—Nopal Red, Plate 1, lightly overcast with Carmine, Plate 1. Reverse of petals—Citron Yellow, Plate 16, lightly overcast with Nopal Red, Plate 1.

*Petals.*—Texture—medium. Form.—double.

Fragrance: Characteristic chrysanthemum.

Plant:

*Form.*—Upright; bushy.

*Growth.*—Free.

Foliage:

*Size.*—Medium.

*Quantity.*—Normal.

*Color.*—Upper side—Cress Green, Plate 31. Reverse side—Light Elm Green, Plate 17.

*Texture.*—Leathery.

I claim:

A new and distinct variety of chrysanthemum plant of the incurved type, substantially as herein shown and described, characterized particularly as to novelty by the relatively large size and deep color of its blooms which have a general color tonality of Nopal Red lightly overcast with Carmine, and by the earliness of its blooming habit.

EUGENE S. BOERNER.

No references cited.